United States Patent [19]

Wilkes

[11] Patent Number: 5,549,388

[45] Date of Patent: Aug. 27, 1996

[54] PLEATED STERILIZATION POUCH

[76] Inventor: Kenneth R. Wilkes, 55 Brookwood Rd., Asheville, N.C. 28804

[21] Appl. No.: 445,518

[22] Filed: May 22, 1995

[51] Int. Cl.⁶ .................................................. B65D 30/20
[52] U.S. Cl. .............................. 383/84; 206/438; 383/120
[58] Field of Search ..................................... 206/439, 438; 383/84, 120, 85, 86, 5; 229/80, 80.5

[56] References Cited

U.S. PATENT DOCUMENTS

| | | | |
|---|---|---|---|
| 3,062,371 | 11/1962 | Patience | 206/63.2 |
| 3,070,225 | 12/1962 | Schwartz | 206/56 |
| 3,754,700 | 8/1973 | Bonk | 229/62 |
| 4,276,982 | 7/1981 | Sibrava | 383/84 |
| 4,318,506 | 3/1982 | Hirsch | 383/120 |
| 4,468,811 | 8/1984 | Shaw et al. | 383/84 |
| 4,510,621 | 4/1985 | Sak et al. | 383/89 |
| 4,759,643 | 7/1988 | Canno | 383/84 |
| 4,911,560 | 3/1990 | Hoover et al. | 383/120 |
| 4,932,791 | 6/1990 | Vetter | 383/5 |
| 5,150,971 | 9/1992 | Strong et al. | 229/80 |

FOREIGN PATENT DOCUMENTS

| | | | |
|---|---|---|---|
| 1505539 | 12/1967 | France | 229/80 |
| 1486465 | 6/1969 | Germany | 383/120 |
| 886251 | 4/1961 | United Kingdom. | |
| 2145997 | 4/1985 | United Kingdom | 383/5 |

Primary Examiner—Stephen P. Garbe
Attorney, Agent, or Firm—Saul Epstein

[57] ABSTRACT

A pouch to hold sterile articles which is comprised of two sheets in face to face contact and sealed around the periphery except at an access opening. One of the sheets has one or more pleats which intersect the access opening in order to provide greater internal storage space. A flap on the unpleated sheet overhangs the edge of the pleated sheet, and is covered with a self-adhesive which extends partly into the pouch between the sheets at said access opening. This construction results in both sides of the pleated sheet being in contact with self-adhesive when the flap is folded over the pleated sheet to seal the pouch. In a second embodiment, the pleat intersects the access opening at an angle other than 90 degrees in order to provide a seal at the pleat having greater sterile integrity.

19 Claims, 4 Drawing Sheets

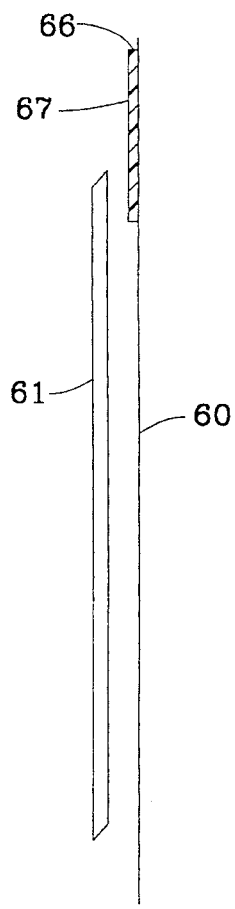
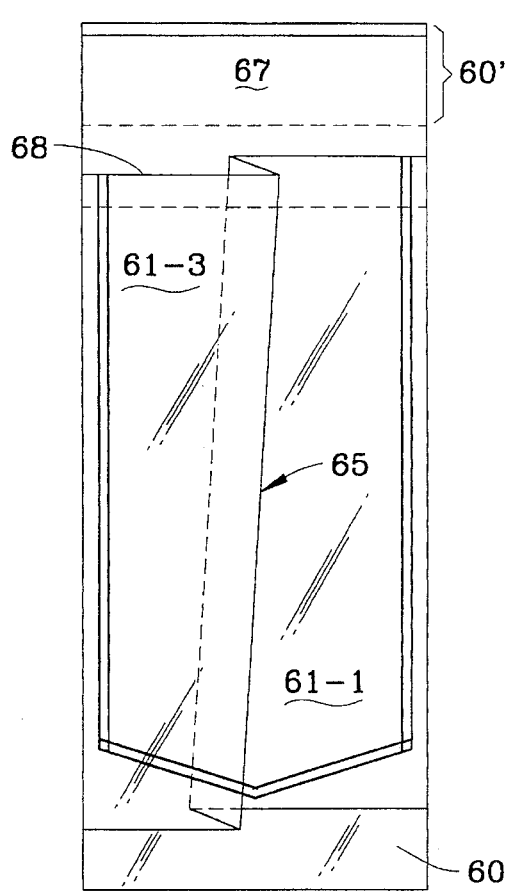
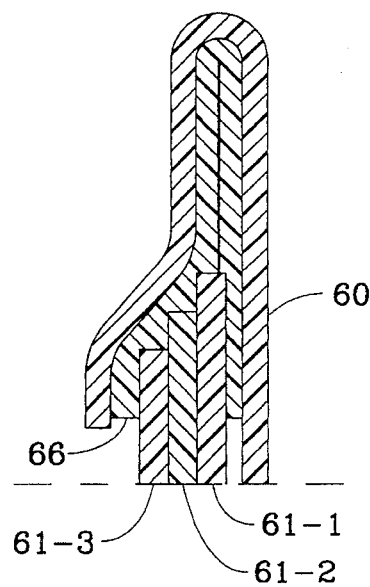
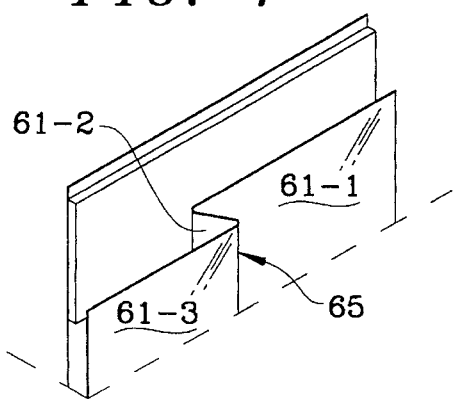
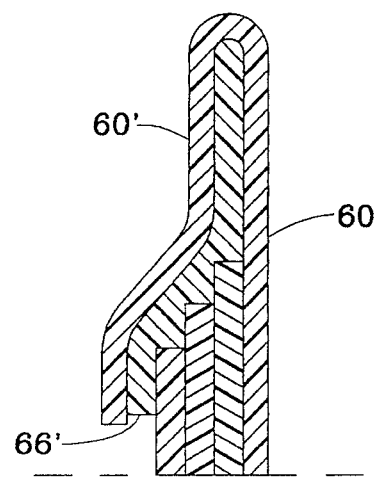

PLEATED STERILIZATION POUCH

BACKGROUND OF THE INVENTION

Plastic pouches used to sterilize and store sterile items for dental and medical use have been available for many years. Such pouches often consist of two similarly sized rectangular sheets in face to face contact, sealed around their periphery. At the time the pouch is manufactured, only three edges are sealed, leaving an access opening to insert items to be stored at a later date. The fourth seal, to seal the access opening, is made after the item to be kept sterile has been inserted into the pouch. After the item to be stored is inserted in the pouch, and the pouch sealed, the item in the pouch is sterilized by steam autoclaving or by using another sterilizing gas such as ethylene trioxide (ETO). In either case, maintaining the item in a sterile state until use depends on the package being adequately sealed to prevent the entry of bacteria.

The three edge seals made at the time of manufacture of the pouch are usually made by applying heat and pressure along relatively narrow lines near the edges to be sealed. The fourth seal, made after the pouch is loaded, may also be a heat seal, but often heat sealing equipment is not available at the location where the pouch is loaded. In particular, many health care offices, including offices of both doctors and dentists, do not have the equipment for making heat seals; hence, for these locations other sealing systems must be used to seal the pouch.

Pouches to be loaded and sealed where heat sealing equipment is not available are generally made to be sealed adhesively. Adhesively sealed pouches for this application are commonly made with one sheet overhanging the other in a manner similar to an envelope flap. The flap is covered with self-adhesive which, at the time the pouch is to be sealed, is folded over the access opening such that the adhesive covers the opening. So long as the two components of the pouch are flat sheets, such construction has been found to be satisfactory. However, the capacity of pouches made of flat sheets is somewhat restricted, and it would be desirable to have gussets or pleats in one of the sheets to allow the pouch to expand and thereby hold larger items. If pleats were to be included in prior art pouches, it would be found that there are three thicknesses of material at the pleat, which are difficult to seal with an adhesive covered flap. In order to create a seal at the pleat, the adhesive must seal to the edge of all three thicknesses of material, which is not likely to occur consistently. Hence, such a pouch would be considered to be unreliable as a container for sterile articles.

SUMMARY OF THE INVENTION

The presently preferred embodiments of the herein described invention include two flexible substantially rectangular sheets in face to face contact, sealed to each other around three edges, with the fourth being left open to receive a product to be stored. One of the sheets, called a "base sheet" is flat, whereas the other sheet, called the "face sheet" has one or more pleats which intersect the open edge of the pouch. The pleat(s) allow the pouch to expand to hold larger objects than if both sheets were flat. The base sheet extends beyond the end of the face sheet at the open edge in a manner similar to an envelope flap.

The flap is coated with self-adhesive which, when folded over the opening, seals the opening. In a first embodiment of the invention disclosed, the self-adhesive extends into the opening under the face sheet as well as covering the exposed flap, so that both sides of the face sheet are in contact with adhesive when the flap is folded over the opening. Having the adhesive seal to both sides of the face sheet makes possible a relatively reliable seal for the fourth edge of the pouch, since with such construction it is not necessary that the end of the ply of the pleat adjacent the base sheet be sealed to achieve pouch integrity;

To make the seal even more reliable, a second embodiment of the invention is disclosed wherein the pleat intersects the open edge of the pouch at an angle other than 90 degrees. So doing provides a surface for the adhesive to seal against rather than an edge, which makes a more dependable seal.

BRIEF DESCRIPTION OF THE DRAWINGS

FIG. 4 shows the pouch after it has been sealed.

FIG. 5 is a plan view of a second embodiment of a pouch embodying the present invention.

FIG. 6 is a side view of the pouch of FIG. 5. The view is partially exploded for clarity.

FIG. 7 is an perspective view of the open end of the pouch of FIG. 5. The view is partially exploded for clarity.

FIG. 8 is a cross sectional view of the end of the pouch shown in FIG. 6, taken at 8—8 of FIG. 6. FIG. 8 shows the pouch after it has been sealed.

FIG. 9 is a cross sectional view of the end of a pouch similar to that shown in FIG. 8, except that the self-adhesive on the flap of the pouch illustrated in FIG. 9 does not extend into the area between the base and face sheets. FIG. 9 shows the pouch after it has been sealed.

FIG. 11 shows the pouch after it has been sealed.

DETAILED DESCRIPTION OF THE INVENTION

Figure 1:
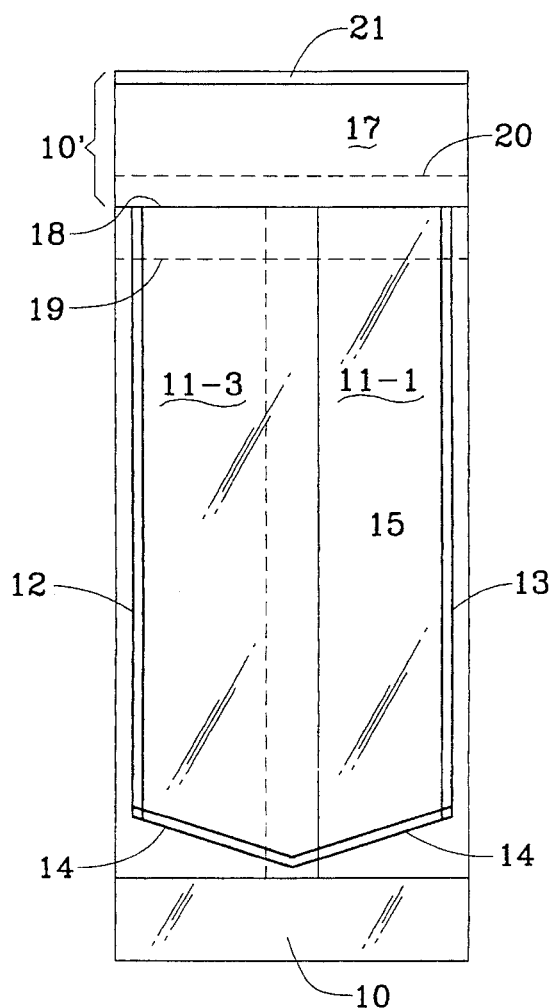
FIG. 1 is a plan view of a pouch embodying the present invention.
Figure 2:
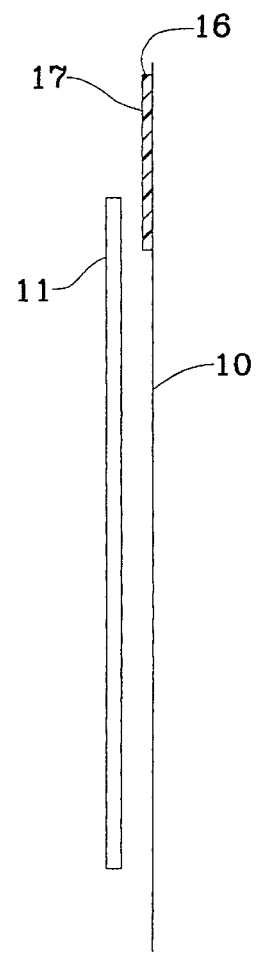
FIG. 2 is a side view of the pouch of FIG. 1. The view is partially exploded for clarity.
Figure 3:
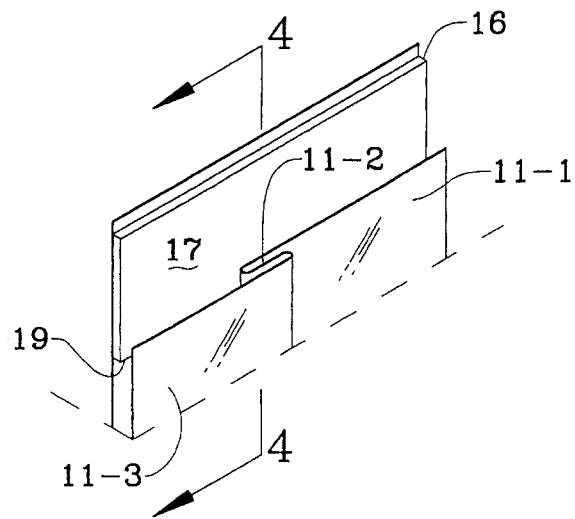
FIG. 3 is an perspective view of the open end of the pouch of FIG. 1. The view is partially exploded for clarity.
Figure 4:
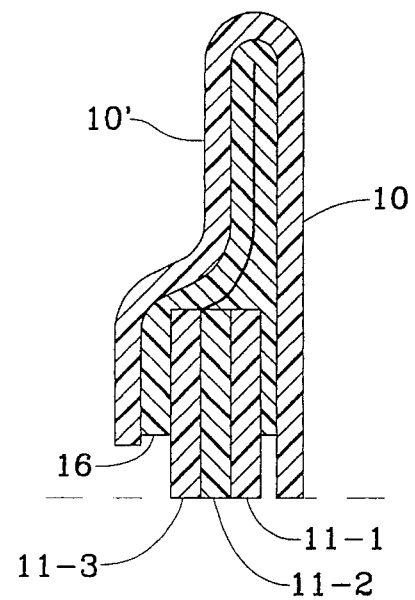
FIG. 4 is a cross sectional view of the end of the pouch shown in FIG. 3, taken at 4—4 of FIG. 3.

The pouch illustrated in FIG. 1 is known in the trade as a "chevron" pouch because of the shape of the seal at one end. It basically consists of two sheets, base sheet 10 and face sheet 11, in face to face contact, and sealed around three edges with heat seals 12, 13, and 14. The seals can be single line seals or preferably, as illustrated, each formed of two or more spaced parallel line seals. Heat seals are made by applying heat and pressure in the areas intended to be sealed. A pleat 15, which intersects the open edge of the pouch (i.e., the edge 18 of the face sheet 11), is formed in face sheet 11. For purposes of explanation, face sheet 11 is divided into three portions, 11-1, 11-2, and 11-3. These portions form the plies of pleat 15, 11-1 being the inner ply, 11-2 being the middle ply, and 11-3 being the outer ply.

A portion of base sheet 10 extends beyond the edge 18 of face sheet 11 to form a flap 10' which, as will be described below, will be folded over face sheet 11 after the pouch is loaded, to make the final seal.

There are many compatible and suitable materials from which the walls of the pouch could be made, but for illustrative purposes, base sheet 10 could be made of high porosity surgical grade kraft paper having a caliper of 3.5 to 4 mils, and face sheet 11 could be 48 gauge polyester laminated to 1.5 mil polypropylene film. Sheets made of these materials can easily be sealed to each other with heat seals, as is well known in the art. For clarity, sheets 10 and 11 are shown spaced from each other in the partially exploded figures, but it will be appreciated that in an actual pouch they are in contact.

A coating of a self-adhesive 16 occupies at least a portion of the area of flap 10', and also extends some distance into the area between base sheet 10 and face sheet 11 (to edge 19 in the embodiment illustrated). The self-adhesive 16 (which may conveniently be about 2 mils thick) is covered with a release liner 17 which can be peeled off after the pouch is loaded, to expose the adhesive. Normally, the adhesive 16 and the release liner 17 are purchased in the form of what is known as "self-seal tape" and applied to the base sheet 10 as a single item during manufacture of the pouch. The adhesive in this product is coated onto the release liner, and extends to its edge. At the time of use, the release liner can be peeled away, and the adhesive will remain on the base sheet. In order to assure the sterile integrity of the pouch, it is important that release liner 17 at edge 19 not overhang the edge of the underlying adhesive. It has been found that the self-adhesive on self-seal tape provides an adequate seal to heat seals 12 and 13 (which cross edge 19). The release liner material is such that no seal will be formed between it and face sheet 11 when heat seals 12 and 13 are made, even though the the heated iron which forms the heat seals extends over release liner 17 (as indicated on FIG. 1). Since many of the users of pouches of the type being described in this specification will desire to autoclave the pouch after loading, it is preferred that the self-seal tape, and the other components of the pouch, be autoclavable.

It is preferred that a lip 21 of base sheet 10 extend beyond the edge of release liner 17 in order to facilitate the peeling of the release liner from the base sheet when the pouch is to be sealed. Also, a score 20 is preferably provided in flap 10' to provide a guide for folding the the base sheet over to make the final seal.

By making the area of self-adhesive extend under the face sheet 11, as can be seen in FIGS. 1–4, the necessity of sealing the ends of the plies at the interface between plies 11-1 and 11-2 is avoided. The path to the interior of the pouch by contaminants entering between plies 11-1 and 11-2, and proceeding over edge 18, and then between base sheet 10 and ply 11-1 is blocked by the self adhesive between base sheet 10 and ply 11-1.

Self-adhesive has a special affinity for other self-adhesive, and hence the construction described above would improve the sealing properties of a pouch as described above, even if there were no pleats in the face sheet.

A second embodiment of the invention is illustrated in FIGS. 5–8, which creates an even more positive seal for the pouch. Base sheet 60, self-adhesive 66, and release liner 67 are similar to the corresponding elements of the first embodiment. The pleat 65 in face sheet 61, however, is not at right angles to the end 68 of the face sheet as in the first embodiment. In the first embodiment of the invention discussed above, the integrity of the pouch depends upon a seal being made to the end of the face sheet at the middle ply of the pleat. While reasonably reliable, as discussed, an even more reliable seal would result if the seal were to be made to a surface of the sheet, rather than to an end. By making the pleat 65 intersect the end 68 of face sheet 61 at an angle other than 90 degrees, as can be seen in FIG. 6, a sealing surface is created at the pleat on the top of the middle ply 61-2 and the inner ply 61-1. The deviation from 90 degrees need not be very much, angles of the order of about one degree from the vertical have been found to be sufficient. The angle shown in the figures is exaggerated for clarity.

The creation of surfaces against which to seal in the pleat area, results in an adequate seal even if the self-adhesive 66 does not extend under the face sheet. This alternative is illustrated in FIG. 9 where self-adhesive 66' is shown as being only in the area 60' of the base sheet, and not extending under the face sheet. FIG. 9 shows the end of a pouch similar to that illustrated in FIGS. 5–7 except that the self-adhesive does not extend into the area between the face and base sheets. The figure shows the pouch after it has been sealed.

Figure 10:
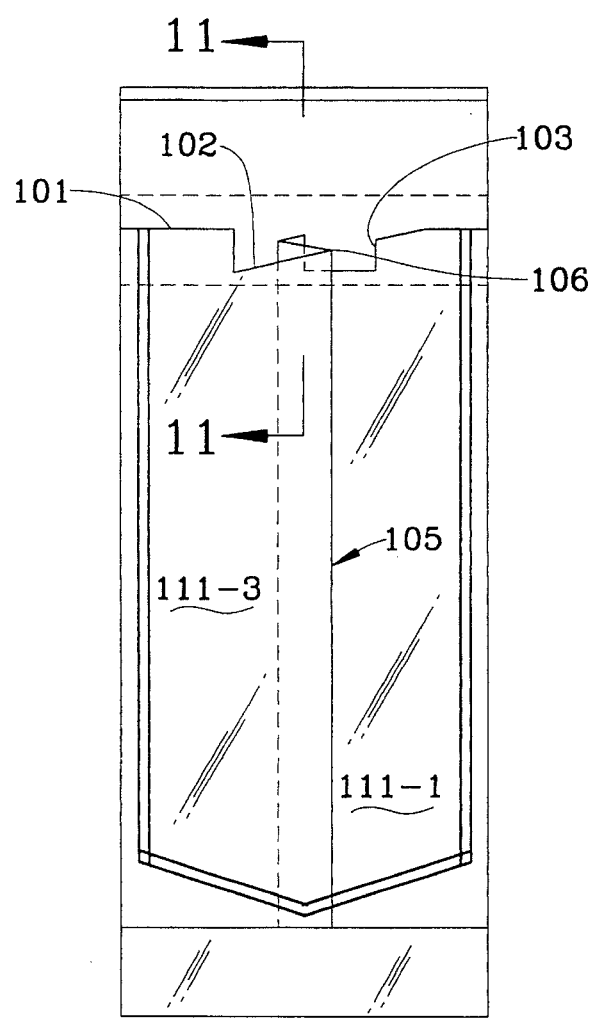
FIG. 10 is a plan view of a variant of the pouch of FIG. 6.
Figure 11:
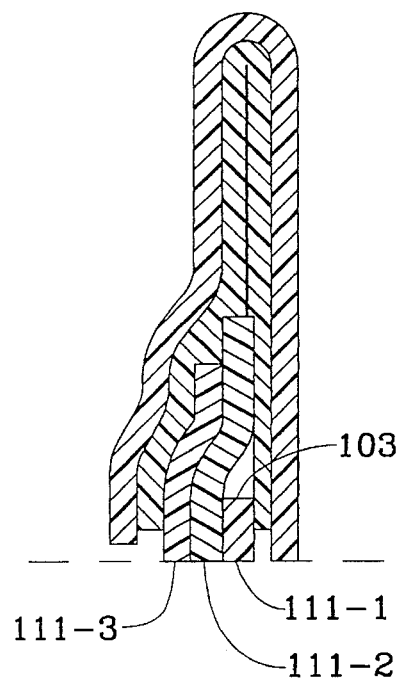
FIG. 11 is a cross sectional view of the end of the pouch shown in FIG. 10, taken at 11—11 of FIG. 10.

FIGS. 10 and 11 illustrate a variant of the embodiment shown in FIGS. 5–8. The pleat 105, as shown in FIG. 10 is square with the edge 101 of face sheet 111 (the pleat being formed of plies 111-1, 111-2, and 111-3). The angularity which causes there to be a surface on each ply of the pleat for the adhesive to adhere to is created by making a triangular cutout 102 on the edge of the sheet. An additional feature shown is cutout 103 (shown as rectangular, but is not necessarily so). Cutout 103 (which could as well be applied to the embodiment of FIGS. 5–8 if desired) provides an extra measure of security at the "outer" corner 106 of pleat 105. The term "outer" indicates that it is the corner of the pleat away from, as opposed to against, the base sheet. The triangular cutout 102 can be used with or without the cutout 103. It will be appreciated that while triangular cutout 102 is shown as extending only partially across the width of the pouch, there need be no edge 101 at all, and a non-square edge 102 could extend completely across the width of the pouch and have the same effect.

Figure 13:
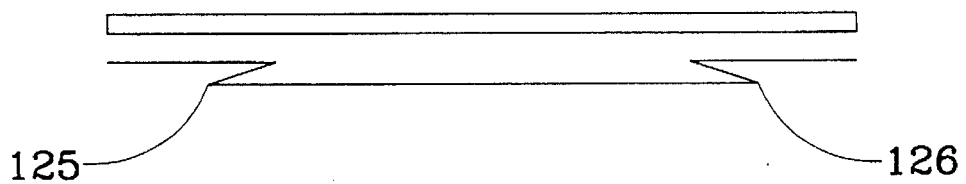
FIG. 13 is an end view of the pouch of FIG. 12, exploded for clarity.
Figure 12:
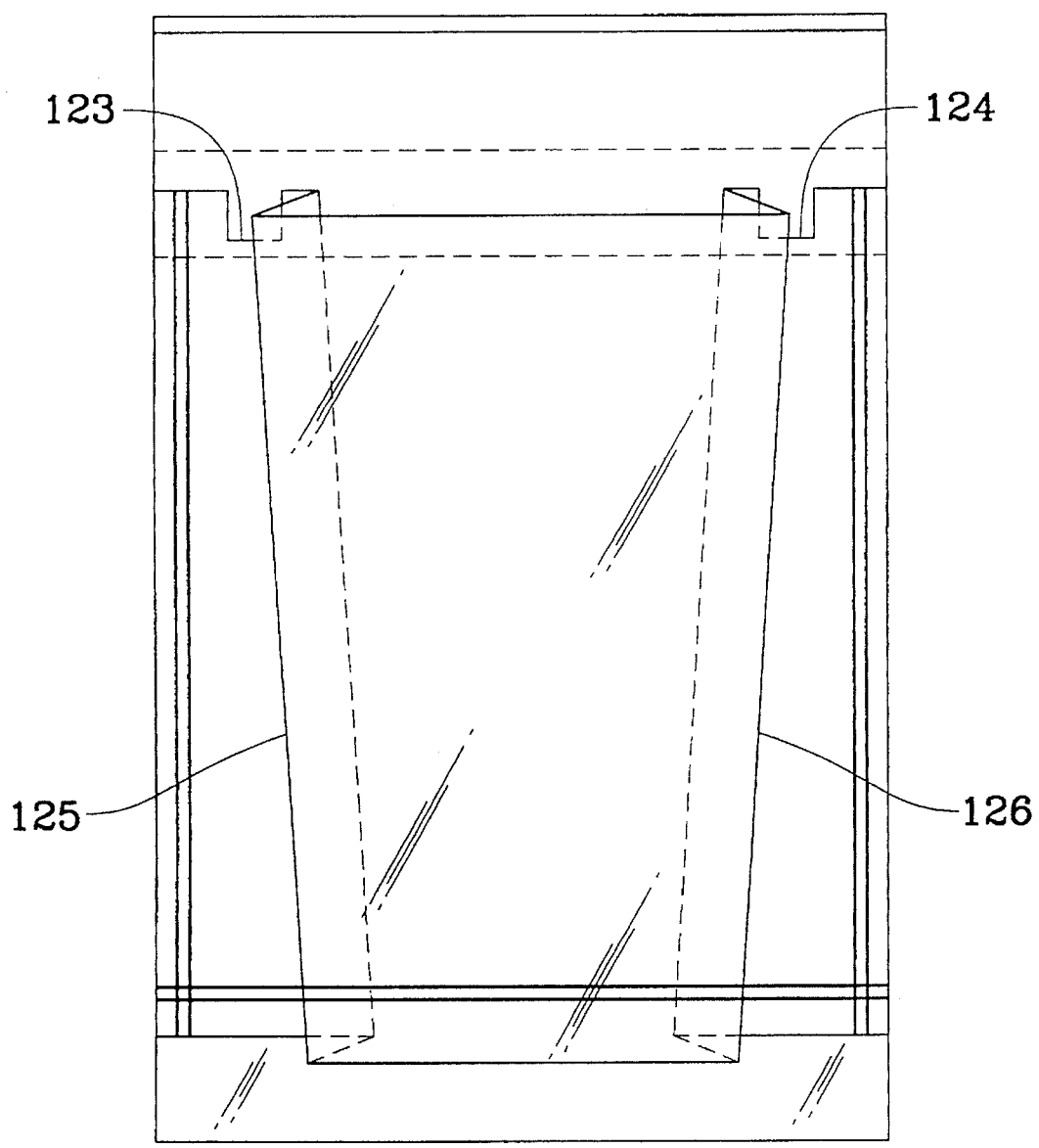
FIG. 12 is a plan view of a pouch similar to that of FIG. 6, but having two pleats.

FIGS. 12 and 13 illustrate a pouch utilizing the principles of the present invention which includes two pleats 125 and 126, rather than only one, and wherein the pleats are angled as shown in FIG. 6, and also including cutouts 123 and 124 in the edge of the facing sheet to provide extra security at the outside corners of the pleats, as discussed in connection with FIG. 10. It may be noted that as shown in FIG. 12, the pleats face oppositely, but they could as easily face the same direction, if desired. As before, the angle of the pleats is exaggerated for illustrative purposes.

I claim:
1. A sealable pouch which comprises:
    a base sheet having a pouch area and a flap area;
    a face sheet in face to face contact with said base sheet, and covering said pouch area of said base sheet, said face sheet being sealed around its periphery to said base sheet to form a pouch, but leaving one edge adjacent said flap area of said base sheet unsealed as an access opening;
    one or more pleats in said face sheet intersecting said unsealed edge of said face sheet, said pleats comprising at least an inner ply, a middle ply, and an outer ply, the intersection of said pleats with said unsealed edge being such that an exposed sealing area on the face of each of said plies exists adjacent said unsealed edge; and a coating of self-adhesive on said base sheet covering at least a portion of said flap area of said base sheet, and extending into said pouch area whereby said self-adhesive covers a portion of said base sheet between said face sheet and said base sheet adjacent said access opening.

2. A sealable pouch as recited in claim 1 where the edge of said face sheet at said access opening and at least one of said pleats intersect at other than a right angle.

3. A sealable pouch as recited in claim 2 where said face sheet is substantially rectangular, and at least one of Said pleats are not parallel to an edge of said face sheet.

4. A sealable pouch as recited in claim 3 where the angle between said at least one of said pleats and the edge of said face sheet most closely parallel to said pleat is about one degree or more.

5. A sealable pouch as recited in claim 2 where said angle is about 89 degrees or less.

6. A sealable pouch as recited in claim 2 where the edge of said face sheet at said access opening is cut away in an area of said inner ply surrounding the intersection of said middle ply and said outer ply at said access opening of at least one of said pleats.

7. A sealable pouch as recited in claim 6 where said angle is about 89 degrees or less.

8. A sealable pouch as recited in claim 1 and further including a release liner covering said self-adhesive.

9. A sealable pouch as recited in claim 8 where said seals are made by applying heat and pressure between said base and face sheets along one or more lines adjacent to the periphery of said sheets to form heat seals, said heat seals intersecting said coating of self-adhesive.

10. A sealable pouch as recited in claim 9 where the edge of said face sheet at said access opening and at least one of said pleats intersect at other than a right angle.

11. A sealable pouch as recited in claim 10 where said angle is about 89 degrees or less.

12. A sealable pouch as recited in claim 1 and further including a cutout in the edge of said face sheet where at least one of said pleats intersects said edge whereby said at least one of said pleats intersects said edge at an angle other than a right angle.

13. A sealable pouch as recited in claim 12 where said angle is about 89 degrees or less.

14. A sealable pouch which comprises:

a base sheet having a pouch area and a flap area;

a face sheet in face to face contact with said base sheet, and covering said pouch area of said base sheet, said face sheet being sealed around its periphery to said base sheet to form a pouch, but leaving one edge adjacent said flap area of said base sheet unsealed as an access opening, said face sheet having one or more pleats comprised of at least an inner ply, a middle ply, and an outer ply, said plies intersecting said unsealed edge of said face sheet so as to leave an exposed sealing area on the face of each of said plies adjacent said unsealed edge; and a coating of self-adhesive on said base sheet covering at least a portion of said flap area of said base sheet.

15. A sealable pouch as recited in claim 14 where said pleats intersect said unsealed edge of said face sheet at other than a right angle and said angle is about 89 degrees or less.

16. A sealable pouch as recited in claim 14 where the edge of said face sheet at said access opening is cut away in an area of said inner ply surrounding the intersection of said middle ply and said outer ply at said access opening of at least one of said pleats.

17. A sealable pouch as recited in claim 16 where said pleats intersect said unsealed edge of said face sheet at other than a right angle and said angle is about 89 degrees or less.

18. A sealable pouch as recited in claim 14 and further including a release liner covering said self-adhesive.

19. A sealable pouch as recited in claim 18 where said seals are made by applying heat and pressure between said base and face sheets along one or more lines adjacent to the periphery of said sheets to form heat seals, said heat seals intersecting said coating of self-adhesive.

\* \* \* \* \*